United States Patent
Lin

(10) Patent No.: US 6,197,801 B1
(45) Date of Patent: Mar. 6, 2001

(54) INJECTABLE PHARMACEUTICAL COMPOSITION FOR TREATMENT AND REVERSAL OF ERECTILE DYSFUNCTION

(75) Inventor: An-Hao Lin, West Covina, CA (US)

(73) Assignee: USA Doctors Products, Inc., Las Vegas, NE (US)

( * ) Notice: Subject to any disclaimer, the term of this patent is extended or adjusted under 35 U.S.C. 154(b) by 0 days.

(21) Appl. No.: 09/321,693

(22) Filed: May 28, 1999

Related U.S. Application Data

(63) Continuation-in-part of application No. 09/110,814, filed on Jul. 6, 1998, now abandoned, which is a continuation-in-part of application No. 09/007,166, filed on Jan. 14, 1998, now abandoned, and a continuation-in-part of application No. 09/007,142, filed on Jan. 14, 1998, now abandoned.

(51) Int. Cl.[7] .................. A61K 31/425; A61K 31/19; A61K 31/20; A61K 31/47
(52) U.S. Cl. .................. 514/365; 514/573; 514/559; 514/307
(58) Field of Search .................. 514/365, 573, 514/559, 307

(56) References Cited

PUBLICATIONS

Yajima, Michitaka; "Effects of vasoactive drugs on the isolated rabbit corpus cavernosum of the penis"; Nippon Hinyokika Gakkai Zassh (1989), 80 (10), 1422–9; ISSN 0021–5287, 1989.*

* cited by examiner

Primary Examiner—Theodore J. Criares
Assistant Examiner—Jennifer Kim

(57) ABSTRACT

An injectable pharmaceutical composition for treatment of erectile dysfunction. The composition includes prostaglandin E-1, and optionally further includes levsin and/or additional vasodilators such as diltiazem HCl, verapamil, chlorpromazine, d,L-hyoscyamine, and 6,7-dimethoxy-1-veratrylisoquinoline HCl. The composition is effective for long-term restoration of normal erectile function to a patient having erectile dysfunction. The ability to reverse erectile dysfunction may be further enhanced by the inclusion of vitamin B-6, B-12, folic acid, and/or TPA. Also disclosed are methods for treatment and reversal of erectile dysfunction by injecting the pharmaceutical composition into the penis, either by subcutaneous or intracavernosal injection.

20 Claims, No Drawings

INJECTABLE PHARMACEUTICAL COMPOSITION FOR TREATMENT AND REVERSAL OF ERECTILE DYSFUNCTION

This is a continuation-in-part of U.S. application Ser. No. 09/110,814, filed Jul. 6, 1998 now abandoned, which is a continuation-in-part of U.S. application Ser. No. 09/007,166, filed Jan. 14, 1998 now abandoned. This application is also a continuation-in-part of U.S. application Ser. No. 09/007,142, filed Jan. 14, 1998 now abandoned. The contents of all of the above applications are incorporated herein by reference.

FIELD OF THE INVENTION

The present invention relates to pharmaceutical compositions for treatment of erectile dysfunction. The invention also relates to methods of administering the compositions for treatment of erectile dysfunction, including by subcutaneous (sub-q), intramuscular (IM), intracavernosal (IC), intravenous (IV), and intraarterial injection. The invention further relates to methods for reversal of erectile dysfunction by administering the compositions disclosed herein to a patient in order to improve penile circulation, which has the long-term benefit of restoring erectile function well after administration of the compositions of the invention.

BACKGROUND OF THE INVENTION

Erectile dysfunction is a serious condition which afflicts a significant percentage of the male population worldwide. This condition often has significant psychological effects which can, in severe cases, significantly reduce the quality of life for the person affected. The effects are often most severe among elderly male patients, but this condition has become increasingly prevalent within the middle-aged, and even the youthful segments of the male population.

It is believed that the parasympathetic nerve plays an important role in the regulation of erectile function. As noted above, impotence is most frequent in the elderly male population. Impotence is also a frequent affliction among male patients who have undergone prostatectomy, either for treatment of prostate cancer or an enlarged prostate condition. In fact, although numerous patients are candidates for removal of enlarged prostate, many elect not to have the surgery, and to live with the effects of an enlarged prostate, because they fear loss of normal erectile function. In addition to prostatectomy, several other causes have been linked to erectile dysfunction, including diabetes, psychological causes, surgery (including lower back which affects the parasympathetic nerve), trauma, obesity, smoking, or any other condition which constricts or restricts the arteries or reduces blood flow.

There are currently five methods available for treatment of erectile dysfunction. First, a prostaglandin-E1 product (Muse, Vivus) is available for intra urethral administration. Injectable products include products comprising prostaglandin-E1 for intramuscular/intracavernosal injection. None of these products interact with all of the important receptors or with the parasympathetic nerve. In fact, injectable products including only prostaglandin-E1 have been shown to have an efficacy of no greater than 50%. Moreover, none of these products have shown any efficacy for reversal of erectile dysfunction, and therefore injection or administration must be repeated each time an erection is desired. Further drawbacks of these injectable preparations are that they produce pain and unnatural erection, in addition to the difficulties of injection. In addition to these pharmaceutical treatments for erectile dysfunction, implants have also been used for treatment of erectile dysfunction. These include both permanently rigid implants (e.g., Erectaid), as well as implants having pumping capabilities, and which therefore can be deflated after use.

Thus, a product is needed for treatment of erectile dysfunction having an efficacy of greater than 50%. Moreover, a product is needed for reversal of erectile dysfunction, a product for which one or a few administrations will restore to the patient normal erectile function. Moreover, a pharmaceutical product is needed for treatment of impotence in male patients who have undergone prostatectomy, surgery (including lower back which affects the parasympathetic nerve), trauma, or who suffer from diabetes, psychological causes of impotence, obesity, smoking, or any other condition which constricts or restricts the arteries or reduces blood flow.

SUMMARY OF THE INVENTION

The present invention relates to injectable pharmaceutical compositions as described below for treatment of erectile dysfunction. We have discovered that prostaglandin E-1, in combination with other agents disclosed herein, can be used successfully as a vasodilator for treatment of erectile dysfunction, and even for reversal to cause recovery from erectile dysfunction. Thus, in certain embodiments, the preparation includes prostaglandin E-1 in an amount effective to cause erection in a patient experiencing erectile dysfunction. In another embodiment the preparation will include additional vasodilators, such as antimuscarinics, e.g., d,L-hyoscyamine and/or dicyclomine HCl. In other embodiments the preparation will include further vasodilators, such as calcium channel blockers, e.g., verapamil and/or diltiazem HCl. In other embodiments the preparation will also include levsin and/or additional vasodilators, such as smooth muscle relaxants, e.g., 6,7-dimethoxy-1-veratrylisoquinoline HCl. In other embodiments the preparation will also include chlorpromazine, a pharmaceutical having vasodilating action due to its effect on the autonomic nervous system and direct action on blood vessels.

The invention also relates to preparations which include one or more agents to enhance the ability of the preparation to reverse erectile dysfunction by providing long-term improvement of penile circulation. For example, the injectable pharmaceutical composition of the invention may include vitamin B-12, vitamin B-6, folic acid, and/or tissue plasminogen activator.

The methods of the invention include methods for treatment of a patient having erectile dysfunction, and determination of reversal of erectile dysfunction. The physician provides a pharmaceutical composition having an effective amount of prostaglandin E-1, and optionally further having effective amounts of one or more of levsin, verapamil and 6,7-dimethoxy-1-veratrylisoquinoline HCL. The patient is injected with the pharmaceutical composition. The injection will typically occur in the penis, but may also occur elsewhere in the body. Injection may be subcutaneous, intracavernosal or intramuscular, and may also occur systemically (i.e., intravenous or intra-arterial).

Before, during, and after injection, the patient may be diagnostically monitored to determine the increase in penile hemodynamic function (circulation), in order to quantitatively or semi-quantitatively determine the effectiveness of treatment or reversal of erectile dysfunction. Any diagnostic technique useful to monitor or detect perfusion or blood circulation may be used. Useful techniques include ultrasound, MRI, CT, and X-ray (fluoroscopy), and any of these techniques may further include the use of contrast agents which are well known and commercially available. Techniques for measuring hemodynamic parameters include those disclosed in Place, U.S. Pat. No. 5,482,039, incorporated herein by reference.

In other methods of the invention, the pharmaceutical composition will further include effective amounts of additional vasodilating agents, such as diltiazem HCl, d,L-hyoscyamine, dicyclomine HCl, chlorpromazine. In still other methods, the composition will include one or more agents which enhance the ability of the preparation to reverse erectile dysfunction by providing long-term improvement of penile circulation. These compositions thus effect treatment which restores normal erectile function to the patient. For example, the injectable pharmaceutical composition may include effective amounts of vitamin B-12, vitamin B-6, folic acid, and/or tissue plasminogen activator.

DETAILED DESCRIPTION

In a first embodiment the injectable pharmaceutical compositions for treatment of erectile dysfunction includes prostaglandin E-1 in an amount effective to cause an erection in a patient experiencing erectile dysfunction. In another embodiment the preparation will also include levsin and/or additional vasodilators, such as verapamil, and may optionally further include 6,7-dimethoxy-1-veratrylisoquinoline HCl. The effective amount of prostaglandin E-1 will typically be 0.0001–60 μg, more preferably 0.001–60 μg, more preferably 0.01–60 μg, more preferably 0.1–60 μg, more preferably 0.5–20 μg, more preferably 1.0–10 μg. When included, the effective amount of verapamil will typically be 0.001–10 mg, more preferably 0.05–5 mg, more preferably 0.1–1 mg. When included, the effective amount of 6,7-dimethoxy-1-veratrylisoquinoline HCl will typically be 0.0001–60 mg, more preferably 0.001–10 mg, more preferably 0.01–1 mg, more preferably 0.1–0.5 mg. All of these pharmaceuticals are commercially available and the sources are known to those of skill in the art.

In other embodiments the preparation will include any of the above compositions in combination with an effective amount of levsin, which will typically be 0.0001–10 mg, more preferably 0.0005–1 mg, more preferably 0.001–0.5 mg. Levsin (hyoscyamine sulfate USP) is one of the principal anticholinergic/antispasmodic components of belladonna alkaloids. The empirical formula is (C17H23NO3) 2.H2SO4.2HO2 and the molecular weight is 712.85. Chemically, it is benzeneacetic acid, alpha-(hydroxymethyl)-,8-methyl-8-azabicyclo(3.2.1.)oct-3-yl ester,(3(S)- endo)-,sulfate(2:1),dihydrate. Levsin inhibits specifically the actions of acetylcholine on structures innervated by postganglionic cholinergic nerves and on smooth muscles that respond to acetylcholine but lack cholinergic innervation. These peripheral cholinergic receptors are present in the autonomic effector cells of the smooth muscle, the cardiac muscle, the sinoatrial node, the atrioventricular node, and the exocrine glands. At therapeutic doses, it is completely devoid of any action on autonomic ganglia. Levsin inhibits gastrointestinal propulsive motility and decreases gastric acid secretion. Levsin also controls excessive pharyngeal, tracheal and bronchial secretions.

In other embodiments the preparation will include any of the above compositions in combination with one or more further vasodilating agents such as diltiazem HCl in an amount of 0.0001–50 mg, more preferably 0.001–1 mg, more preferably 0.01–0.5 mg; d,L-hyoscyamine in an amount of 0.0001–10 mg, more preferably 0.0005–1 mg, more preferably 0.001–0.5 mg; dicyclomine HCl in an amount of 0–40 mg, more preferably 0.1–20 mg, more preferably 0.5–10 mg, more preferably 1–5 mg; or chlorpromazine in an amount of 0.0001–50 mg, more preferably 0.001–10 mg, more preferably 0.01–8 mg, more preferably 1–5 mg.

Thus, in one embodiment, the composition is a vasodilating amount (10–80%) of prostaglandin-E1. In another embodiment, the composition further includes an effective amount (5–20%) of an antimuscarinic agent (such as dicyclomine HCl or d,L-hyoscyamine). In other embodiments, the composition includes any of the above compositions (prostaglandin-E1 or prostaglandin-E1 and antimuscarinic) in combination with an effective amount (10–50%) of a calcium channel blocker (such as verapamil or diltiazem HCl, or other calcium blocker). In still other embodiments, the composition comprises any of the above compositions in combination with an effective amount (5–20%) of a smooth muscle relaxant (such as 6,7-dimethoxy-1-veratrylisoquinoline HCl). In still other embodiments, the composition comprises any of the above compositions in combination with an effective amount (5–20%) of an agent which acts on the autonomic nervous system, such as chlorpromazine.

In the most preferred embodiment, the composition includes all five different classes of compounds (vasodilator, antimuscarinic, calcium channel blocker, smooth muscle relaxant, and an agent which acts on the autonomic nervous system) in a pharmaceutical preparation. When this pharmaceutical preparation is injected into the penile muscle body (corporal), it causes an increase in blood supply to the penis. Ten to fifteen minutes after injection, an erection results with the ability to penetrate during intercourse. This preparation also works to prevent premature ejaculation.

In other embodiments the preparation will cure erectile dysfunction by repeated use over a period of time. Thus, administration of one injection per week for 2 months, more preferably 3 months, more preferably 4 months, more preferably 5 months, more preferably 6 months or more, will cause long-term improvement in penile circulation and thus reversal of erectile dysfunction. More preferably, administration will include two injections per week for 2 months, more preferably 3 months, more preferably 4 months, more preferably 5 months, more preferably 6 months or more. More preferably, administration will include three injections per week for 2 months, more preferably 3 months, more preferably 4 months, more preferably 5 months, more preferably 6 months or more. More preferably, administration will include four injections per week for 2 months, more preferably 3 months, more preferably 4 months, more preferably 5 months, more preferably 6 months or more. In other embodiments the preparation will include one or more agents which enhance the ability of the preparation to reverse erectile dysfunction by providing long-term improvement of penile circulation. For example, the injectable pharmaceutical composition may include vitamin B-12 in an amount of 0–10 mg, more preferably 0.1–10 mg, more preferably 0.5–8 mg, more preferably 1–5 mg; vitamin B-6 in an amount of 0.0001–10 mg, more preferably 0.001–1 mg, more preferably 0.010–0.8 mg, more preferably 0.1–0.5 mg; folic acid in an amount of 0.0001–10 mg, more preferably 0.001–0.8 mg, more preferably 0.01–0.6 mg; and/or tissue plasminogen activator in an amount of 0–1 mg, more preferably 0.1–0.8 mg, more preferably 0.30–6 mg.

The pharmaceutical preparations may be formulated neat, or using any of a number of pharmaceutical carriers, diluents, or excipients well known in the art. For details, the reader is referred to the Remmington catalog, incorporated herein by reference. For example, in certain cases, a pharmaceutical carrier of benzyl alcohol, chlorobutanol, sodium chloride, Bacteriostatic water, and normal saline is used. The injectable composition will typically have a total volume of approximately 0.0005–1 cc, more preferably 0.001–0.5 cc, more preferably 0.01–0.1 cc. A volume of 0.01 cc will suffice to give a 50 min erection. In certain other embodiments, the pharmaceutical compositions will comprise oral tablets, such as for example capsules, caplets, gel caps, syrup, swallow tablets, chewable tablets, and the like.

The methods disclosed herein are for treatment of a patient having erectile dysfunction. The methods include the steps of providing a pharmaceutical composition having an effective amount of prostaglandin E-1, and optionally further having effective amounts of one or both of verapamil and 6,7-dimethoxy-1-veratrylisoquinoline HCL. The patient is injected with the pharmaceutical composition. The injection will typically occur in the penis, but may also occur elsewhere in the body. Injection may be subcutaneous, intramuscular, or intracavernosal, and may also occur systemically (i.e., intravenous or intra-arterial). For intracavernosal injection a one-third inch needle penetration is sufficient.

In other methods, the pharmaceutical composition will further include effective amounts of additional vasodilating agents, such as diltiazem HCl, d,L-hyoscyamine, dicyclomine HCl, chlorpromazine. In still other methods, the composition will include one or more agents which enhance the ability of the preparation to reverse erectile dysfunction by providing long-term improvement of penile circulation. These compositions thus effect treatment which restores normal erectile function to the patient. For example, the injectable pharmaceutical composition may include effective amounts of vitamin B-12, vitamin B-6, folic acid, and/or tissue plasminogen activator.

The compositions disclosed herein are characterized in that they are at least about 60% effective for treatment of erectile dysfunction, whereas existing pharmaceutical preparations are no more than 50% effective. Preferred compositions disclosed herein are at least about 70% effective for treatment of erectile dysfunction, more preferably at least about 80% effective, more preferably at least about 90% effective, more preferably at least about 95% effective. The compositions herein are characterized in that they stimulate the parasympathetic nerve for improvement of erectile function. The disclosed compositions moreover act on one or more receptor cites for vasodilation, more preferably two or more receptors, more preferably three or more receptors, more preferably four or more receptors, most preferably five or more receptors. The disclosed compositions are also characterized in that they are effective for treatment of impotence associated with prostatectomy, surgery (including lower back which affects the parasympathetic nerve), trauma, diabetes, psychological causes of impotence, obesity, smoking, or any other condition which constricts or restricts the arteries or reduces blood flow.

EXAMPLE 1

A first pharmaceutical composition suitable for either intramuscular, intracavernosal, or subcutaneous injection is prepared to include the following materials:

| | |
|---|---|
| prostaglandin E-1 | 50 μg |
| verapamil | 0.1 mg |
| 6,7-dimethoxy-1-veratrylisoquinoline HCl | 90 mg |
| d,L-hyoscyamine | 0.1 mg |
| chlorpromazine | 0.2 mg |
| benzyl alcohol | 0.445% w/v |
| chlorobutanol | 0.5% |
| sodium chloride | 0.5 mg |
| Bacteriostatic water | 1 mL |
| total volume | 1 mL |

EXAMPLE 2

A second pharmaceutical composition suitable for either intramuscular, intracavernosal, or subcutaneous injection is prepared to include the following materials:

| Ingredient | Total Used mL in mg. | Total Used per mL | 1 unit [100 units = 1 mL] |
|---|---|---|---|
| chlorpromazine | 3/75 | 5.357143 | 0.0536 |
| d,L-hyoscyamine | 3/1.2 | 0.085714 | 0.0009 |
| diltiazem HCl | 2/10 | 0.714286 | 0.0071 |
| 6,7-dimethoxy-1-veratrylisoquinoline HCl | 6/180 | 12.85714 | 0.1286 |
| prostaglandin E-1 | 40 mcg | 2.857143 | 0.0286 |
| Total | 14 | | |

According to this formula, 0.01 cc will suffice to give a 50 minute erection. This preparation is also effective for treatment of premature ejaculation.

EXAMPLE 3

A preparation made according to Example 1 was administered to a 43-year-old male patient LD with a history of premature ejaculation. A 0.1 cc dose of formulated solution was injected intracavernosally into the penis. He experienced continuous sexual activity for 3 hours.

EXAMPLE 4

A preparation made according to Example 1 was administered to a 47-year-old male patient EH. The patient had experienced, over a period of 2–3 years, a gradual decline in his ability to maintain an erection for the entire duration of intercourse. He experienced a 6-hour erection (i.e., priapism) after injection of 0.23 cc formulated solution intracavernosally into the penis. Moreover, this treatment with the formulated solution actually restored his ability to maintain a strong erection for the entire duration of intercourse on subsequent occasions, even without having further injections. Thus, IC administration of the formulation disclosed herein demonstrated a reversal of erectile dysfunction.

EXAMPLE 5

A preparation made according to Example 1 was administered to a 48-year-old male patient WL. He experienced a 2-hour erection after injection of 0.27 cc formulated solution intracavernosally into the penis.

EXAMPLE 6

A preparation made according to Example 1 was administered to a 47-year-old obese male patient PP. He experienced a 1-hour erection after injection of 0.20 cc formulated solution intracavernosally into the penis.

EXAMPLE 7

A preparation made according to Example 1 is administered to a 50-year-old male patient having a history of prostate inflammation and having undergone prostate removal. He experiences a 1-hour erection after injection of 0.20 cc formulated solution intracavernosally into the penis.

EXAMPLE 8

A preparation made according to Example 1 is administered to a 50-year-old male patient. He experiences a 1-hour erection after injection of 0.20 cc formulated solution subcutaneously into the penis.

EXAMPLE 9

A preparation made according to Example 2 is administered to a male patient. He experiences a 1-hour erection after injection of 0.01 cc formulated solution IC into the penis.

EXAMPLE 10

A preparation made according to Example 2 is administered to a male patient. He experiences a 6-hour erection after injection of 0.01 cc formulated solution IC into the penis.

EXAMPLE 11

Two male patients, AA and BB, are selected, both suffering from impotence. Penile circulation is monitored by ultrasound to determine baseline circulation readings. A preparation made according to Example 1 is administered to AA by intracavernosal injection into the penis. Patient BB receives intracavernosal injection of placebo. Penile circulation is again monitored by ultrasound to determine enhanced circulation readings at t=0. Each week AA and BB are tested in this same manner, and pre- and post-injection circulation readings are recorded. The study is continued for 6-months. After 6-months, injections are discontinued, and only ultrasound recordings are continued for an additional 6-month period.

The results of this study are as follows. During the first 6-month period, pre-injection circulation readings are consistently higher for AA than for BB, with the exception of the readings at t=0. Moreover, the difference between circulation readings for AA and BB increases with each succeeding week. During the second 6-month period, circulation readings are consistently higher for AA than for BB. The difference between circulation readings for AA and BB remains approximately constant.

While particular compositions and methods have been described herein, once this description is known, it will be apparent to those of ordinary skill in the art that other embodiments and alternative steps are also possible without departing from the spirit and scope of the invention. Moreover, it will be apparent that certain features of each embodiment as well as features disclosed in each reference incorporated herein can be used in combination with features illustrated in other embodiments. Accordingly, the above description should be construed as illustrative, and not in a limiting sense, the scope of the invention being defined by the following claims.

What is claimed is:

1. An injectable pharmaceutical composition for treatment of erectile dysfunction, comprising:

0.0001–60 μg prostaglandin E-1;

0.0001–10 mg levsin;

0.0001–60 mg 6,7-dimethoxy-1-veratrylisoquinoline HCl;

0.0001–50 mg diltiazem HCl; and 0.0001–50 mg chlorpromazine.

2. The injectable pharmaceutical composition of claim 1, further comprising verapamil.

3. The injectable pharmaceutical composition of claim 1, wherein the diltiazem HCl is in an amount of 0.0001–30 mg.

4. The injectable pharmaceutical composition of claim 1, further comprising 0.1–40 mg dicyclomine HCl.

5. The injectable pharmaceutical composition of claim 1, wherein the chlorpromazine is in an amount of 0.0001–50 mg.

6. The injectable pharmaceutical composition of claim 1, further comprising 0.1–10 mg vitamin B-12.

7. The injectable pharmaceutical composition of claim 1, further comprising 0.0001–10 mg vitamin B-6.

8. The injectable pharmaceutical composition of claim 1, further comprising 0.0001–10 mg folic acid.

9. The injectable pharmaceutical composition of claim 1, further comprising tissue plasminogen activator.

10. The injectable pharmaceutical composition of claim 1, further comprising a pharmaceutical carrier comprising benzyl alcohol and normal saline.

11. The injectable pharmaceutical composition of claim 10, wherein the composition is in the form of a solution having total volume of approximately 0.0005–1 cc.

12. A method for treatment of a patient having erectile dysfunction, comprising the steps of:

providing a pharmaceutical composition comprising 0.0001–60 μg prostaglandin E-1 and 0.0001–10 mg levsin; and injecting the patient with the pharmaceutical composition.

13. The method of claim 12, wherein the treatment restores normal erectile function to the patient.

14. The method of claim 12, wherein the injection is subcutaneous.

15. The method of claim 12, wherein the injection is intracavernosal.

16. The method of claim 12, wherein the pharmaceutical composition further comprises 0.1–10 mg vitamin B-12.

17. The method of claim 12, wherein the pharmaceutical composition further comprises 0.0001–10 mg vitamin B-6.

18. The method of claim 12, wherein the pharmaceutical composition further comprises 0.0001–10 mg folic acid.

19. A method for reversing erectile dysfunction in a patient, comprising the steps of:

providing a pharmaceutical composition comprising 0.0001–60 μg prostaglandin E-1 and 0.0001–10 mg levsin; and injecting the patient with approximately one dose of the pharmaceutical composition per week for approximately 2 months.

20. The injectable pharmaceutical composition of claim 1, further comprising 0.0001–60 mg 6,7-dimethoxy-1-veratrylisoquinoline HCl.

\* \* \* \* \*